(12) United States Patent
Holsteyns et al.

(10) Patent No.: US 7,016,028 B2
(45) Date of Patent: Mar. 21, 2006

(54) METHOD AND APPARATUS FOR DEFECT DETECTION

(75) Inventors: Frank Holsteyns, Blanden (BE); Francesca Iacopi, Leuven (BE); Karen Maex, Herent (BE)

(73) Assignee: Interuniversitair Microelektronica Centrum (IMEC), Leuven (BE)

( * ) Notice: Subject to any disclaimer, the term of this patent is extended or adjusted under 35 U.S.C. 154(b) by 67 days.

(21) Appl. No.: 10/458,405

(22) Filed: Jun. 9, 2003

(65) Prior Publication Data

US 2004/0246472 A1    Dec. 9, 2004

Related U.S. Application Data

(60) Provisional application No. 60/386,695, filed on Jun. 7, 2002.

(51) Int. Cl.
*G01N 21/88* (2006.01)
(52) U.S. Cl. .................................. 356/237.1
(58) Field of Classification Search .. 356/237.1–237.6, 356/601, 625, 636; 250/559.26, 559.27, 250/559.19, 559.4, 559.44
See application file for complete search history.

(56) References Cited

U.S. PATENT DOCUMENTS 4,314,474 A    2/1982 Dermarderosian ............. 73/15

2001/0030296 A1 * 10/2001 Ishimaru et al. ......... 250/559.4

FOREIGN PATENT DOCUMENTS

FR    1516884    2/1968
WO    WO 00/12999    3/2000

OTHER PUBLICATIONS

"Wafer Level Detection of Sealing Defects," Quoc Toan Le, Frank Holsteyns, Francesca Iocopi, and Karen Maex, Abstract submitted for a presentation at the MRS Spring 2003 conference held Apr. 21-25, 2003.
European Search Report for Application No. 03447145.8-1524—dated Oct. 18, 20004.

* cited by examiner

*Primary Examiner*—Tu T. Nguyen
(74) *Attorney, Agent, or Firm*—McDonnell Boehnen Hulbert & Berghoff LLP

(57) ABSTRACT

A method for determining the presence of defects in a covering layer overlying an underlying layer in accordance with an embodiment of the invention comprises providing a substrate comprising the covering layer, where the covering layer is at least partially exposed. The covering layer is subjected to a first substance, such as a solvent, and then subjected to a light beam. An optical property of the covering layer is determined and compared with a threshold value. The presence of defects in the covering layer is determined by the difference of the optical property from the threshold value, where the optical property indicates a level of penetration of the first substance through the covering layer.

21 Claims, 3 Drawing Sheets

METHOD AND APPARATUS FOR DEFECT DETECTION

CROSS REFERENCE TO RELATED APPLICATIONS

This application claims priority benefits under 35 U.S.C. § 119(e) to U.S. Provisional Patent Application No. 60/386,965, filed on Jun. 7, 2002. The entire disclosure of U.S. Provisional Application No. 60/386,965 is hereby incorporated by reference.

FIELD OF THE INVENTION

The present invention relates to a method and apparatus for the detection of defects in a material and, more specifically, to detecting defects in thin films.

BACKGROUND INFORMATION

In semiconductor manufacturing processes, numerous layers may be deposited onto a semiconductor substrate to form, for example, electronic devices and/or circuits. In some cases, such layers are protected against environmental influences, such as, for example, moisture. The layer to be protected may be termed an underlying layer and may be, for example, the substrate itself, a grown layer (such as an oxide), or a deposited layer, among other possibilities. To protect such underlying layers, a protecting layer, which may also be referred to as a covering layer, is deposited on top of an underlying layer so as to protect (e.g. cover) the underlying layer.

Many advanced semiconductor processes also have a need for insulating materials with low dielectric constants (also called k-values). This need arises from the fact that the operational speed of circuits manufactured with such processes is dependent on the impedance of signal lines in the circuit (such as copper lines) and, thus, the dielectric constant of the signal lines and any insulating material surrounding the signal lines. High performance circuits, therefore, have a need for ever-improved materials. Presently, it is preferable that such materials have dielectric constants of 2.0 or lower. Development of such low-k dielectric materials is motivated by a desire to reduce capacitance, e.g. capacitance between interconnects and signal lines in ultra large-scale integrated circuits (ICs), as such capacitance is typically adverse to circuit performance. Furthermore, reducing such capacitance also reduces crosstalk (e.g. signal interference) between adjacent signal lines, an increasingly severe problem in advanced processes due to the close proximity of such signal lines to one another. Thus, low-k dielectrics may be used in a broad spectrum of applications that are sensitive to ever-smaller geometries.

One concern with low-k dielectrics is the permittivity of such materials. In this regard, low-k dielectric materials (e.g. organic or inorganic) with relatively low permittivities can exhibit a constitutive porosity and/or a subtractive porosity. Constitutive porosity is typical for materials with k-values on the order of 2.7. Subtractive porosity is typical for materials with a k-value smaller than 2.7, though exceptions may exist. In this respect, materials with low relative permittivity can be very sensitive to the environment to which they are exposed, be it the ambient (e.g. room) environment, the semiconductor processing environment or any environment to which such materials are subjected, whether deliberately or unintentionally. Such exposure could lead to problems with such materials. For example, unwanted process interactions, absorption of molecules, contamination during processing, and mobile ion drift diffusion may occur, as some examples. Such situations typically lead to degradation of such porous material layers, and can lead to an undesirable increase in the dielectric constant of those layers.

It is noted that such low-k dielectric materials are not necessarily porous. However, for non-porous materials, environmental factors, such as exposure to any number of materials (e.g., solvents) during semiconductor processing may cause certain materials to swell, which may damage and/or deteriorate their electrical, physical, chemical and/or mechanical properties. Such damage and/or deterioration may occur, even though the compound to which the layer is exposed does not penetrate into the material.

To avoid a change in a material's k-value due to absorption or adsorption of moisture, gases, liquids, or any other substances during, or between processing steps, the low-k material may be encapsulated (sealed) by one or more covering layers. It is desirable that such a covering layer is applied to substantially the entire exposed surface of such a low-k dielectric material layer.

A covering layer can be deposited as a thin film on the exposed surface of a low-k layer (or other underlying layer) or by treating a porous material to effect pore sealing using, for example, plasma treatment, chemical treatment, deposition of a self assembled monolayer, or from an etch process. In this regard, etching of vias and/or trenches can result in pore sealing. This is due, at least in part, to the plasma treatment and the chemical nature of the plasma. As such, etching as used in the context of the present invention includes plasma treatment and chemical treatment. It is desirable to keep the covering layer as thin as possible in order to keep the overall dielectric constant (of the underlying layer in combination with the covering layer) as low as possible. If the covering layer is too thick, an increase of the dielectric constant will occur.

Porous materials are often used because of their low k-values. It is desirable to keep covering layers on such materials as thin as possible so as not to substantially increase the overall k-value. However, one undesirable consequence of keeping the covering layer on such materials as thin as possible is that the covering layer will be discontinuous and, as a result, certain parts of the underlying layer will not be covered with the covering layer. In this situation, such discontinuities of the covering layer (or the presence of defects in such a layer) may lead to the exposure of the underlying layer (e.g., a low k dielectric layer,) to environmental factors, as was discussed above. Therefore, degradation of the electrical, physical, chemical and/or mechanical properties of the underlying layer may occur in this situation. While thicker covering layers have lower defect rates, they result in an undesirable increase in the overall dielectric constant. Such an increase in the overall dielectric constant may adversely affect the performance of a circuit including such dielectric/covering layer combinations. In view of the foregoing, it is desirable that covering layers are sufficiently thin, yet substantially free from discontinuities and/or defects. In this regard, techniques that are able to monitor for such defects in the covering layer during processing are desirable.

It is also desirable that these techniques be non-destructive, so that such a monitoring technique may be used for quality control purposes in semiconductor manufacturing process. In this regard, if discontinuities and/or defects are detected in a covering layer, another covering layer may be applied on top of the discontinuous/defective covering layer.

Thereafter, such a non-destructive monitoring technique could be employed once again to examine the second covering layer for defects.

Alternatively, such techniques may be used to reject defective materials being processed in a semiconductor processing line. In this case, such defect monitoring techniques could be used to identify and remove, from a semiconductor processing line, electronic devices and/or semiconductor wafers in which covering layers show discontinuities and/or defects, whereas devices and/or wafers without defects in the covering layer are processed further.

SUMMARY

Methods and apparatus for detecting defects in a covering layer are disclosed. Such methods and apparatus provide for locating and/or quantifying defects in a covering layer in order to perform quality control against process acceptance or rejection criteria, such as for wafer acceptance or rejection. Methods and apparatus for determining a sealing efficiency of a specific barrier (e.g. covering layer) to be used on a given dielectric material layer are also disclosed.

An embodiment of a method for determining the presence of discontinuities and/or defects of a covering layer on a semiconductor substrate comprises providing a semiconductor substrate including the covering layer, where the covering layer is at least partially exposed. At least a portion of the covering later is subjected to a first substance and the portion is subjected to a light beam. An optical property of the covering layer is detected, the optical property corresponding to a level of penetration of the first substance through the covering layer. The presence of defects and/or discontinuities is determined by comparison of the optical property with a threshold value. Such a method may be used for quality control testing of the covering layer.

An embodiment of a method for determining the threshold value comprises providing a semiconductor substrate including a covering layer, the covering layer being at least partially exposed. The method also includes subjecting at least part of the covering layer to a second substance (as compared to the first substance discussed above), substantially without exposing the covering layer to the first substance. At least a part of the covering layer is exposed to a light beam. Light scattered by the covering layer is detected and light directly reflected by the covering layer is rejected. The first threshold is then derived based on the detected scattered light.

BRIEF DESCRIPTION OF THE DRAWINGS

The subject matter regarded as the invention is particularly pointed out and distinctly claimed in the claims section concluding this document. The invention, however, both as to organization and method of operation, together with features and advantages thereof, may best be understood by reference to the following detailed description when read with the accompanying drawings in which:

DETAILED DESCRIPTION

Figure 1:
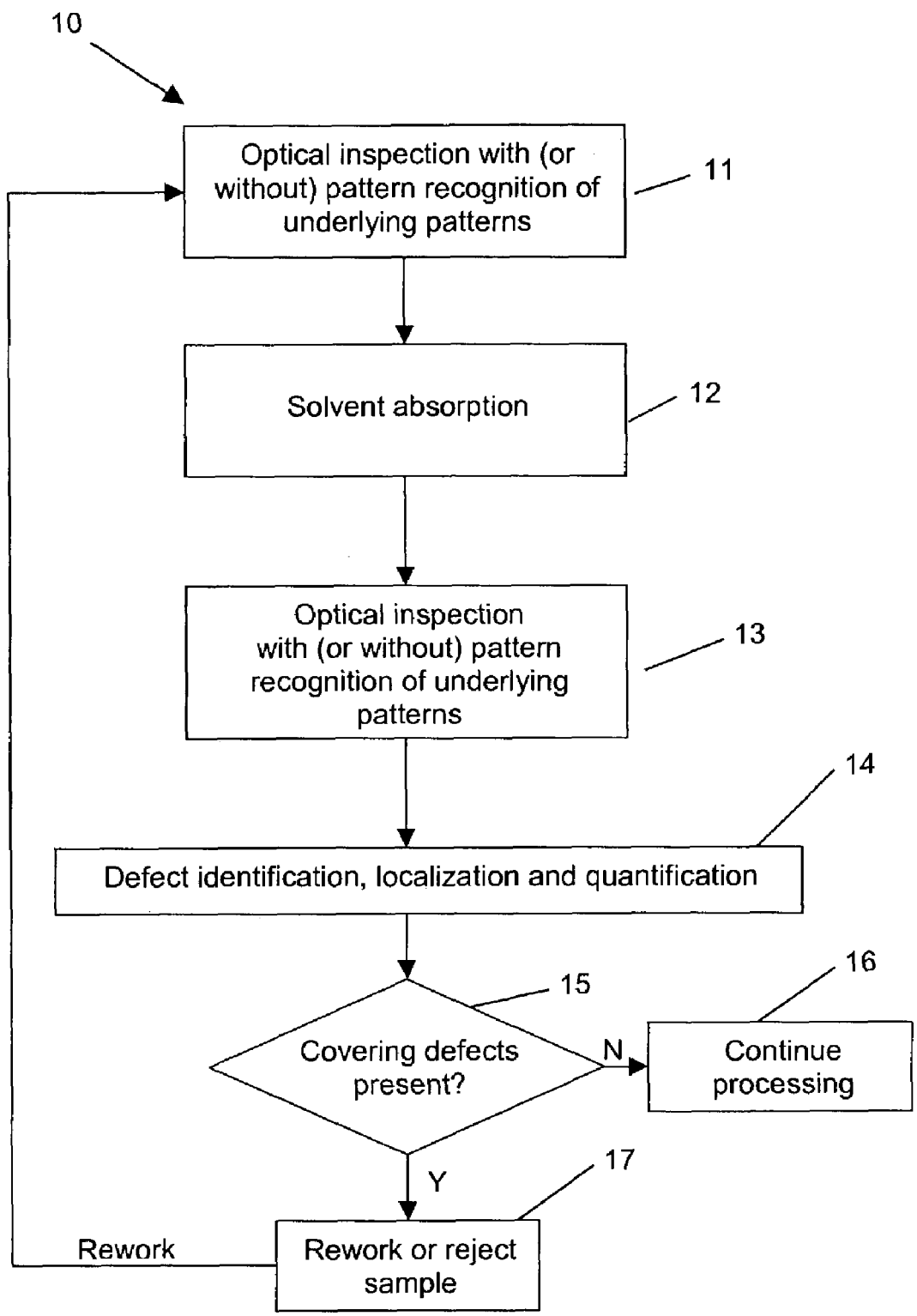
FIG. 1 is a flowchart illustrating a method for the detection of defects in a covering layer according to an embodiment of the invention.

In the following detailed description, numerous specific details are set forth in order to provide a thorough understanding of the invention and how it may be practiced in one or more exemplary embodiments. However, it will be understood that the present invention may be practiced without these specific details. In other instances, well-known methods, procedures and techniques have not been described in detail, so as not to obscure the present invention.

Furthermore, the terms first, second, third and the like in the description and in the claims, are used for distinguishing between similar elements and not necessarily for describing a sequential or chronological order. It is to be understood that the terms, so used, are interchangeable under appropriate circumstances, and that the embodiments of the invention described herein are capable of operation in other sequences than those described and/or illustrated herein.

As was indicated above, methods and apparatus for determining the presence of defects and/or discontinuities (collectively "defects") in a covering layer overlying a substrate and/or underlying layer are disclosed. Such methods and apparatus may be said to determine the integrity or sealing efficiency of such covering layers. In certain embodiments, the term "substrate" may include any appropriate underlying material or materials upon which a device, a circuit or an epitaxial layer may be formed.

In other alternative embodiments, the substrate may comprise a semiconductor substrate such as, for example, doped silicon, gallium arsenide (GaAs), gallium arsenide phosphide (GaAsP), germanium (Ge), or silicon germanium (SiGe), as some examples. The substrate may also include, for example, an insulating layer such as a $SiO_2$ layer or a $Si_3N_4$ layer in addition to the semiconductor substrate portion. Further, the term "substrate" may also include silicon-on-glass and silicon-on sapphire substrates.

Thus, the term substrate is used to generally define a layer (or layers) that underlies (or underlie) a covering layer, such as a porous layer (e.g. a low-k material layer). In this regard, the "substrate" may be any other base on which a layer is formed, for example a glass or metal layer. The substrate may be, for example, a semiconductor substrate that is used in integrated circuit (IC) processing, but is not so limited.

In the following description, the term "processing" will mainly be described with reference to silicon (e.g., semiconductor) processing. However, it will be appreciated that embodiments of the present invention may be employed with other semiconductor material systems.

As was previously discussed, a covering layer is used for covering (sealing) an underlying layer, such as a substrate or an underlying layer that has been deposited onto a substrate. Exemplary embodiments described herein may be employed to detect defects in such covering layers by using an optical, non-destructive approach. These embodiments may be employed during semiconductor processing flows. These embodiments may be employed to evaluate both porous and non-porous material. Thus, their application is not limited to quantifying the integrity (sealing efficiency) of dielectric films exhibiting constitutive and/or subtractive porosity and/or voids or pores related to intentional or non-intentional pores in the material (such as killer voids), which are larger than the expected average pore size.

Exemplary embodiments, as described herein, may also be used for testing the integrity (sealing efficiency) of devices or substrates that comprise a stack of layers, such as, for example, silicon on insulator wafers (e.g., $Si/SiO_2/Si$). When employed in this situation, defects in the upper Si layer due to, for example, hydrofluoric (HF) acid cleaning of the Si, or by deposition of the upper Si layer can be detected. It is noted that the Si layer is not considered a sealing layer, since the underlying layer is not porous, nor subject to swelling in case of contact with a solvent.

Furthermore, the exemplary methods described herein can be used to test the sealing efficiency of air gaps, which are dielectrics comprising substantially 100% air. The exemplary embodiments may also be employed for testing the sealing properties of micro-electromechanical systems (MEMS) or semiconductor device packaging, as two additional examples.

The following is an example of a material system (which may be termed a "sample") with which the exemplary embodiments described herein may be employed. In this regard, an underlying layer is deposited (or formed) on a semiconductor substrate by depositing, for example, a porous layer in any appropriate manner, such as using one of the techniques discussed above. The underlying layer is then covered with a covering layer, which may also be applied in any number of ways. The underlying layer may, for example, be a layer having dielectric properties (such as a material comprising low-k organic (e.g., polymer) or inorganic (e.g., air gap) materials). The covering layer may be, without limitation, an inorganic layer, an organic layer (e.g. a polymer), a metallic layer, or a surface layer that is obtained by surface treatment of the underlying layer. When the covering layer is used as a barrier or a hardmask against environmental factors, the covering layer has to protect the underlying layer efficiently. Therefore, as previously noted, defects in the covering layer are undesirable. In this regard, the quality (sealing efficiency) of the covering layer can be determined by the presence or absence of defects in the layer, which may be termed covering defects. In this regard, detecting covering defects may be made more efficient by noting the primary types of covering defects.

A first type of covering defects is defects caused by particles that are enclosed or embedded in the porous (underlying) layer. These particles may come from the processing ambient environment or may be residual from previous process steps or treatments of the substrate. Such particles typically have a diameter of e.g. 100 nm, while the underlying layer may be very thin and have a thickness of approximately 50 nm.

A second type of covering defects is defects resulting from outliers in the pore structure of the porous (underlying) layer, e.g. non uniform porous volume distribution, non uniform pore size distribution, non uniformity in the deposition of the low-k material, or killer voids in a porous layer, as some examples. Such voids (which are relatively large) can cause incorrect or incomplete coverage by the covering layer.

A third type of covering defects is defects caused by improper or insufficient treatment or application of an insufficient thickness of the covering layer. In this situation, because the deposited covering layer does not have a sufficient thickness, the possibility arises that discontinuities may exist in the covering layer. This may give rise to layers with defects because the underlying layer is not fully covered by the covering layer and, as a result, is exposed to environmental influences.

A fourth kind of defect relates to non-homogeneities in the covering layer. For example, such non-homogeneities include defects in step coverage, asymmetric deposition of the covering layer, and non-uniform deposition of the covering layer (or application of a sealing treatment).

Referring now to FIG. 1, a flowchart that illustrates an exemplary embodiment of a process sequence 10 for detection of defects in a covering layer is shown. Briefly, in accordance with this embodiment, a sample is inspected before and after a solvent absorption process. These inspections allow for differences in light absorption, light scattering and/or light reflection (before and after solvent exposure) to be determined.

Figure 2:
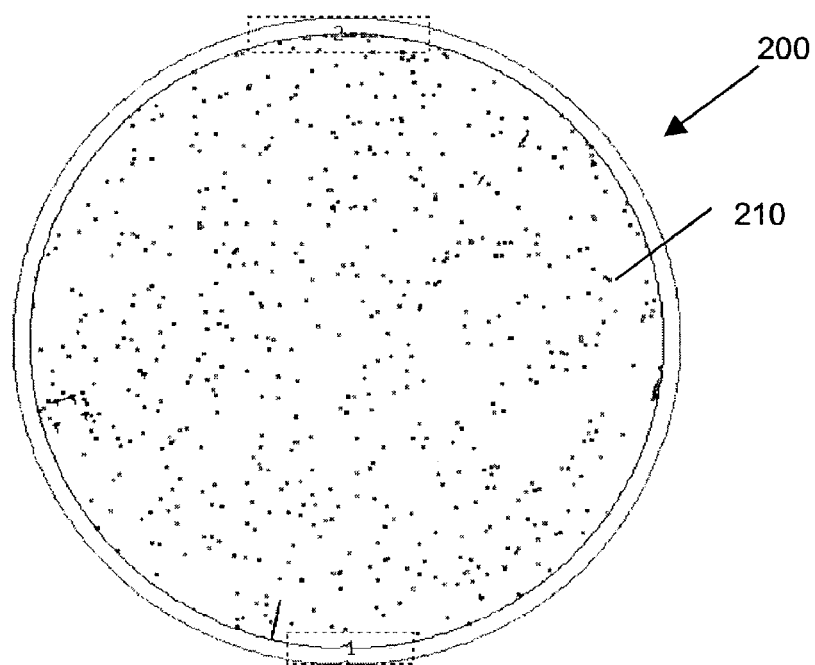
FIG. 2 is a defect map generated based on a scan of a wafer with an oblique incidence light beam, indicating wafer defect locations noted prior to subjecting the wafer to a first substance.

A first inspection of a sample is performed at block 11 of process 10. This first inspection is performed before exposure of the sample to a solvent. During this first inspection, a substantially complete scan of the sample is performed to locate defects, such as those described above. This may be accomplished using a normal light beam or an oblique incident light beam in order to determine, for example, the number of particles present at the surface of the sample. The result of such an inspection for a particular sample is shown in FIG. 2 in the form of a defect map 200. Using such a defect map, the sample surface is mapped, such that location of the particles and/or detected defects 210 is accomplished.

Figure 3A:
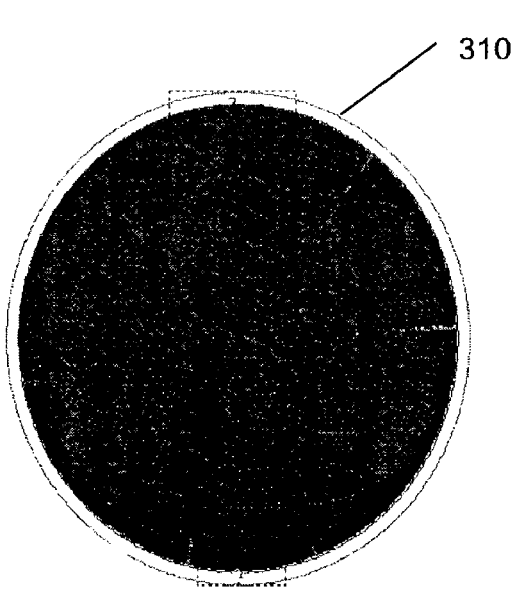
FIGS. 3A–3B are haze maps before (FIG. 3A) and after (FIG. 3B) toluene treatment of the wafer.

At block 12 of the process 10, the sample is scanned again in order to obtain a haze signal of the sample before solvent treatment. Generally, the determination of this haze signal for a particular sample should only be done once. Thereafter, the pre-solvent treatment haze signal is used as a reference. In this regard, the haze signal is a representation of the low frequency signal present in the total scattering signal (e.g., continuous background scattering). Referring to FIG. 3A, an example of a haze map 310 before solvent treatment is shown.

The covering layer of the sample is then subjected to a solvent at block 12 of process 10. In this respect, the covering layer, which comprises at least part of the outermost surface of the sample, is exposed to a liquid, a vapor, or a gas that contains, for example, a solvent. An appropriate solvent is selected, such that exposure of the sample to the solvent is not destructive to the sample. In this regard, the solvent has to be compatible (inert) with the material used as a covering layer and has to provide substantially complete wetting of the covering layer surface. Further, the selected solvent is preferably a highly volatile liquid. The vapor pressure of the liquid or vapor or gas, in one embodiment, may be high enough, such that a high vacuum is not required during exposure of the sample. Typically, non-polar solvents, such as, for example, toluene, hexane, or heptane are used. However, other solvents, such as isopropyl alcohol, ethanol, water or any solvent that, once diffused thorough a defect in the covering layer to the underlying film, leads to a change in the optical properties of the sample may be used.

With respect to solvent selection, organic solvents such as alcohols are not particularly hazardous to work with, do not damage the sample, and are easy and inexpensive to obtain. Additionally, such organic solvents have acceptable vapor pressures, so that a high vacuum is not needed to apply them to the sample. For example, the vapor pressure of toluene at room temperature (approximately 22° C.) is 45 mm Hg.

An additional consideration in solvent selection is the molecule size of the solvent. In this respect, the kinetic diameter of the molecules in the solvent will affect the smallest covering defect that can be detected. For example, for toluene, the kinetic diameter is approximately 0.6 nm.

Solvent absorption (at block 12) may be carried out, for example, by immersing the sample in a solvent solution or by bringing the sample in contact with a solvent vapor. The latter approach may be accomplished by employing a vacuum chamber. For example, the sample is placed in the vacuum chamber, which is then pumped down until the vacuum pressure reaches $10^{-2}$ to $10^{-3}$ Torr. A solvent vapor may then be introduced into the chamber. The covering layer surface is then exposed to the solvent vapor at its saturation pressure at room temperature and for a time sufficient to allow solvent penetration to the underlying (e.g., porous) film through any defects present at the covering layer surface. Typically, such times may range from a few seconds to an hour or more, with shorter exposure times being preferable for process efficiency. The solvent vapor is then pumped out of the chamber after the exposure is complete. The sample is then transferred to an optical inspection tool so as to optically locate and quantify defects revealed by the solvent absorption process.

If covering defects are present, absorption or adsorption of the solvent will take place. Such absorption/adsorption may be identified during an optical inspection step at block 13 of process 10. Places where defects are present in the covering layer and, hence, where the solvent is permitted to penetrate into the covering layer will show a change in one more optical properties. Therefore, by inspection of the sample before solvent exposure at block 11 and inspection after solvent exposure at block step 13, differences in such optical properties may be noted to locate and quantify such covering defects.

In this regard, differences, in coloration may be observed by the naked eye in the case of absorption times between 0 and 15 min for certain defects (such as defects larger than 1 mm). For small defects, with sizes between approximately 100 nm and 1 mm, differences in light scattering may be identified using, for example, a KLA-Tencor SP1$^{DLS}$ apparatus, which is available from KLA-Tencor, One Technology Drive, Milpitas, Calif. Such differences in optical properties may be such that the change in light scattering in the area of such defects after solvent exposure (as compared to light scattering before solvent exposure) exceeds a threshold value, or is less than the threshold value. In this respect, the threshold value corresponds to an amount of scattered light observable before the solvent absorption step.

In the above noted KLA-Tencor apparatus, a sample is scanned with a 488 nm wavelength laser-spot. However, it will be appreciated that any number of light wavelengths can be used. Generally, visible light will be used, but the invention is not so limited. Alternatively, ultraviolet, infrared or x-ray radiation may be used. The light wavelengths used are dependent, at least in part, on the properties of the covering layer and the underlying layer to be inspected, such as by the composition and thickness of the covering layer and underlying layer. Additionally, in an exemplary embodiment, the light beam is a focused or bundled light beam, which is locally applied and moved with respect to the sample. The sizes of the defects that are detectable also depend, at least in part, on the light beam used.

To determine the amount of scattered light, a detector captures the scattered light and communicates it to a photomultiplier. Any directly reflected light is rejected, which may be accomplished through the use of an optical filter. The presence of covering defects may be determined as a result of a difference in light scattering due to the solvent being present in (or at the surface of) the underlying layer. For the exemplary embodiment described above, substantially the entire sample surface is scanned. Such an approach provides for generating a map that indicates the locations on the sample that correspond to different scattering intensities. Thus, detected covering defects can be identified and located by correlating the patterns on the sample, to the particles on the sample, or to any other measurement done on the sample.

Signal processing may be employed to identify, locate and quantify defects from the collected scattered light. Such signal processing techniques are known and will not be described here. Of course, the invention is not limited in scope to any particular signal processing approach.

For the above-described embodiment, the threshold value may be determined by subjecting at least part of the covering layer to a second substance (as compared to the first substance). The second substance may comprise and ambient air environment or, alternatively, a nitrogen ambient. The covering layer is subjected to the first substance prior to (or without substantially) exposing the covering layer to the first substance. The at least a part of the covering layer exposed to the second substance is then exposed to a light beam. Light scattered by the at least a part of the covering layer is detected and light directly reflected by the covering layer is rejected. The first threshold is then derived based on the detected scattered light.

Figure 3B:
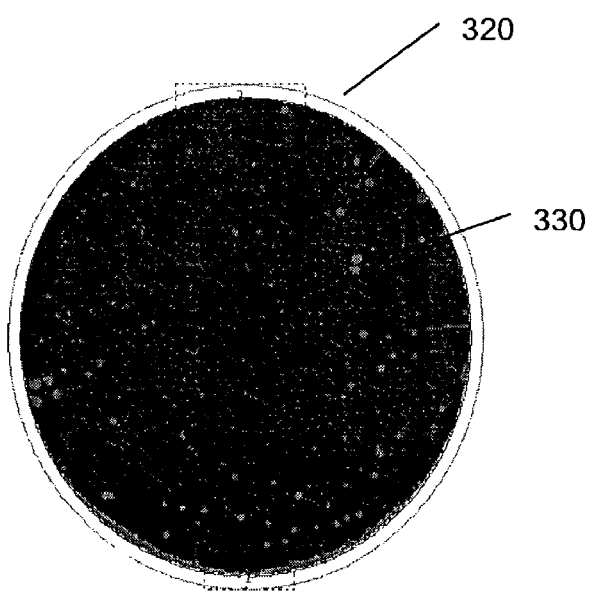

Referring to FIG. 3B, a haze map 320 after solvent treatment is shown. This haze map 320 corresponds with the haze map 310 prior to solvent treatment shown in FIG. 3A. Based on a comparison of the haze map 320 shown in FIG. 3B with the haze map 310 shown in FIG. 3A, covering defects 330 can be distinguished from other defects, located and quantified. The haze map 320 of FIG. 3B may be obtained by filtering out a low frequency signal from a total signal. In this regard, the total scattered light (the total signal) comprises a portion coming from the haze signal (the low frequency signal) and another portion coming from defects (the difference). The haze signal is filtered out, typically with a low-pass filter. It is noted that haze measurements are a standard measurement feature available on the above-mentioned KLA-Tencor SP1$^{DLS}$ apparatus.

Figure 4A:
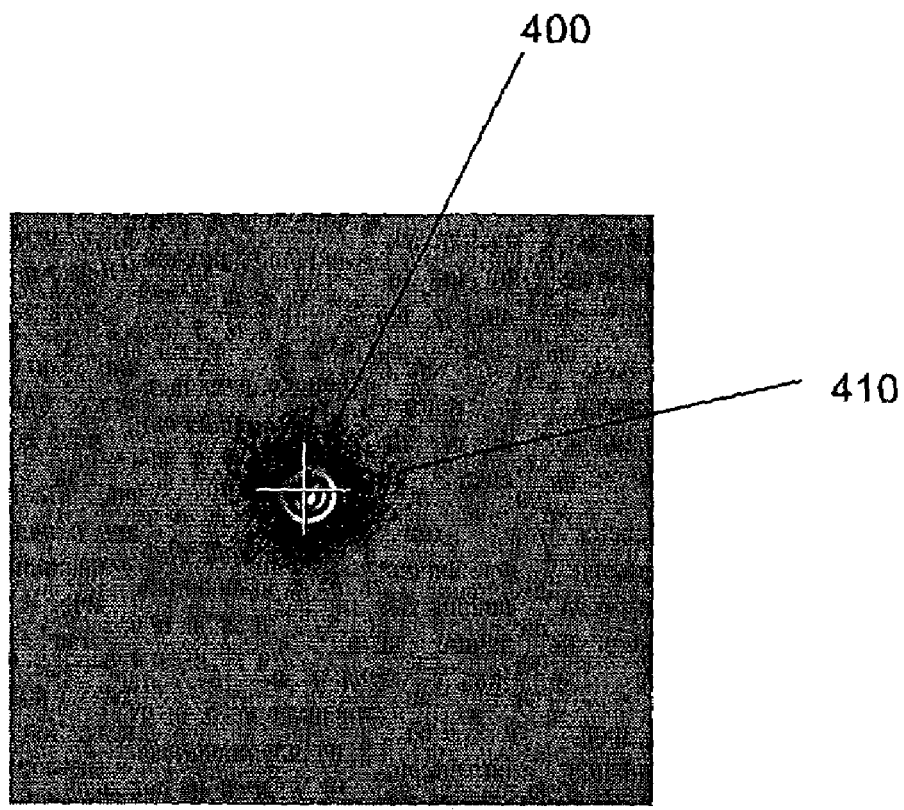
FIGS. 4A–4B are microscopy pictures of a covering layer defect (FIG. 4A) and a normal (underlying layer) defect (FIG. 4B) on the same wafer after toluene treatment according to an embodiment of the present invention.
Figure 4B:
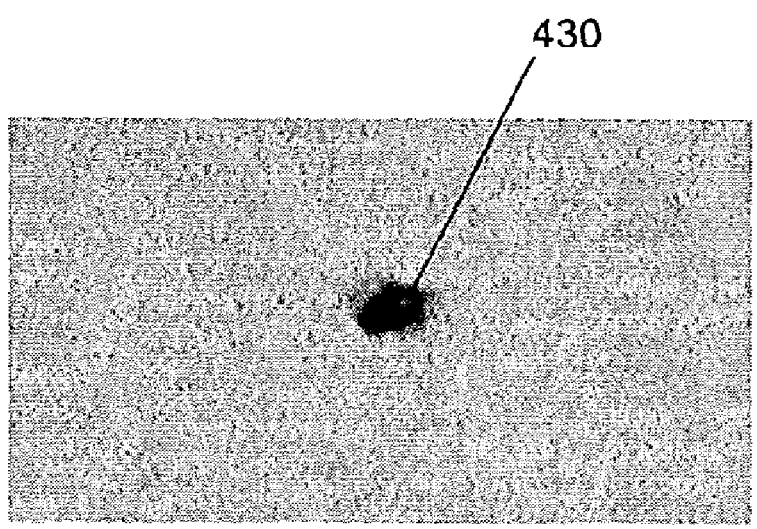

Referring now to FIG. 4, pictures of a covering defect 400 and a normal defect 430 that are present on the same wafer are shown (after solvent treatment), respectively, in FIGS. 4A and 4B. In this context, a "normal" defect is one that is due to a defect in the underlying layer (such as an embedded particle), and not a defect in the covering layer. FIGS. 4A and 4B were generated using an optical microscope. As may be seen in FIG. 4A, the covering defect 400 is surrounded by a halo 420, which is due to the absorption of solvent into the porous underlying layer after diffusing through a covering defect.

Using techniques such as those described above, devices/wafers with covering defects may be identified inline (e.g., during semiconductor processing) such as at block 14 or process 10. When solvent absorption or adsorption occurs, the device has a defective covering layer and is not processed further, and is thus removed from the process flow, such as at blocks 15 and 17 in process. If on the other hand, no solvent absorption takes place, the device can be further processed at block 16 because the covering layer is formed correctly and hence fully protects the underlying layer. Alternatively, samples with certain types of covering defects may be subjected to the application of an additional covering layer or sealing treatment at block 17 and then subjected at to the inspection process 10 shown in FIG. 1. Furthermore, the presence of covering defects may be monitored on a process level and processing parameters may be appropriately adjusted to reduce the occurrence of covering defects.

An exemplary embodiment for detecting covering defects in a particular semiconductor process is now described. In this embodiment, a p-type silicon wafer is used as a substrate. A low-k dielectric material (LKD) with a thickness of approximately 200 nm is deposited on the wafer. The LKD is covered with an approximately 50 nm thick hardmask (covering layer) of SiC. It will be appreciated that any number of materials may be used to form the hardmask, and the invention is not limited in scope to the use of SiC. The hardmask may have a thickness below 200 nm, below 100 nm, or below 50 nm. As previously discussed, it is desirable to keep the hardmask (covering layer) as thin as possible so as not to substantially affect the electrical properties of the underlying layer. In this regard, a monolayer hardmask may be used in certain embodiments.

The wafer may then be inspected for defects, such as at block 11 of FIG. 1 and a defect map (such as shown in FIG. 2) may be generated. The wafer may also be scanned in order to obtain a haze signal for the wafer. This scan may be may be performed (at block 11) in conjunction with the inspection for generating the defect map. Alternatively, the scan may be done separately. The wafer is then placed in a solvent environment, such as a toluene ambient at the vapor pressure of toluene (45 mm Hg) for 5 minutes. Following toluene exposure, optical measurements are performed with the KLA-Tencor SP1$^{DLS}$ over substantially the entire wafer to obtain a post solvent treatment haze map.

In other exemplary embodiments covering layers and underlying layers have been analyzed with the method as described above. In this regard, inorganic layers (e.g. LKD)/polymer layers (e.g. FF02); polymer layer (e.g. silk)/inorganic layer (e.g. SiC); and inorganic layer (e.g. zircon)/metal layer (e.g. Ta) combinations were analyzed. Based on this analysis, it was determine that, the presence of defects in the covering layer may be determined for each of these combinations.

While certain features of the invention have been illustrated and described herein with reference to exemplary embodiments, many modifications, substitutions, changes and equivalents will now occur to those skilled in the art. Therefore, it is to be understood that the appended claims are intended to cover all such modifications and changes as fall within the true spirit of the invention.

What is claimed is:

1. A method for determining the presence of defects in a covering layer overlying an underlying layer comprising:
   providing a substrate comprising the covering layer, the covering layer being at least partially exposed;
   subjecting at least a part of the covering layer to a first substance;
   subjecting at least a part of the covering layer to a light beam;
   detecting at least a haze of the covering layer;
   indicating the presence of defects in the covering layer by determining if at least the haze differs from a first threshold value, the difference indicating a level of penetration of the first substance through the covering layer.

2. The method of claim 1, wherein detecting at least the haze comprises detecting an amount of scattered light and rejecting light directly reflected by the covering layer; and
   wherein indicating the presence of defects in the covering layer comprises determining if at least the haze differs from the first threshold value, the difference indicating the level of penetration of the first substance through the covering layer.

3. The method of claim 1, wherein the covering layer comprises one or more defects, such that the first substance interacts with the substrate.

4. The method of claim 1, wherein the first substance comprises a liquid, a vapor or a gas.

5. The method of claim 1, wherein the first substance comprises an organic solvent.

6. The method of claim 1, wherein the light beam comprises a bundled light beam.

7. The method of claim 1, wherein the light beam comprises one of a visible light beam, an ultraviolet light beam, an infrared radiation beam, and an x-ray beam.

8. The method of claim 1, wherein determining the first threshold value comprises:
   subjecting at least part of the covering layer to a second substance without substantially exposing the covering layer to the first substance;
   subjecting at least a part of the covering layer to a light beam;
   detecting scattered light and rejecting light directly reflected by the covering layer, and
   deriving the first threshold value from the detected scattered light.

9. The method of claim 8, wherein the second substance is air.

10. The method of claim 1, wherein the underlying layer comprises a low dielectric constant material.

11. The method of claim 1, wherein the covering layer substantially covers the underlying layer.

12. The method of claim 11, wherein the covering layer is deposited on the underlying layer.

13. The method of claim 1, wherein the method is used for quality testing of the covering layer.

14. The method of claim 1, further comprising one of accepting and rejecting the layer.

15. The method of claim 1, further comprising changing parameters of a fabricating process for fabricating the covering layer.

16. The method of claim 1, wherein the underlying layer comprises the substrate.

17. An apparatus for determining integrity of a covering layer on a semiconductor substrate the covering layer being at least partially exposed, the apparatus comprising:
   a vessel for subjecting at least a part of the covering layer to a first substance;
   a device for subjecting at least a part of the covering layer to a light beam;
   a photo-detection device for detecting an amount of scattered light and a filter for rejecting light directly reflected by the covering layer; and
   a signal processing device for indicating the presence of defects in the covering layer by determining if at least a haze differs from a first threshold value, the difference indicating a level of penetration of the first substance through the covering layer.

18. The apparatus of claim 17, wherein the first substance comprises a liquid, a vapor or a gas.

19. The apparatus of claim 17, wherein the first substance comprises an organic solvent.

20. The apparatus of claim 17, wherein the light beam comprises a bundled light beam.

21. The apparatus of claim 17, wherein the light beam comprises one of a visible light beam, an ultraviolet light beam, an infrared radiation beam, and an x-ray beam.

* * * * *